US009662423B2

(12) United States Patent
Terry et al.

(10) Patent No.: US 9,662,423 B2
(45) Date of Patent: *May 30, 2017

(54) DEPOSITION OF A SILVER LAYER ON A NONCONDUCTING SUBSTRATE

(71) Applicant: C.R. BARD, INC., Covington, GA (US)

(72) Inventors: Richard Terry, Conyers, GA (US); Fungbor Chen, Covington, GA (US); Zhihui Yin, Liburn, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/184,019

(22) Filed: Feb. 19, 2014

(65) Prior Publication Data

US 2014/0170298 A1    Jun. 19, 2014

Related U.S. Application Data

(63) Continuation of application No. 13/383,535, filed as application No. PCT/US2011/062086 on Nov. 23, 2011.

(60) Provisional application No. 61/417,305, filed on Nov. 26, 2010, provisional application No. 61/421,901, filed on Dec. 10, 2010.

(51) Int. Cl.
| | |
|---|---|
| *A61L 31/08* | (2006.01) |
| *A61L 27/34* | (2006.01) |
| *A61L 27/54* | (2006.01) |
| *A61L 29/08* | (2006.01) |
| *A61L 29/16* | (2006.01) |
| *A61L 31/10* | (2006.01) |
| *A61L 31/16* | (2006.01) |
| *B05D 7/02* | (2006.01) |
| *A61L 29/10* | (2006.01) |
| *A61M 25/00* | (2006.01) |
| *C23C 18/18* | (2006.01) |
| *C23C 18/20* | (2006.01) |
| *C23C 18/42* | (2006.01) |
| *B05D 5/06* | (2006.01) |

(52) U.S. Cl.
CPC ............. *A61L 31/088* (2013.01); *A61L 27/34* (2013.01); *A61L 27/54* (2013.01); *A61L 29/085* (2013.01); *A61L 29/106* (2013.01); *A61L 29/16* (2013.01); *A61L 31/10* (2013.01); *A61L 31/16* (2013.01); *A61M 25/0017* (2013.01); *B05D 7/02* (2013.01); *C23C 18/1882* (2013.01); *C23C 18/1893* (2013.01); *C23C 18/2066* (2013.01); *C23C 18/2086* (2013.01); *C23C 18/42* (2013.01); *A61L 2300/104* (2013.01); *A61L 2300/404* (2013.01); *B05D 5/067* (2013.01); *Y10T 428/31692* (2015.04); *Y10T 428/31707* (2015.04)

(58) Field of Classification Search
CPC ............................. A61K 33/38; A61L 33/088
USPC ............................................ 424/423; 427/2.1
See application file for complete search history.

(56) References Cited

U.S. PATENT DOCUMENTS

| | | | |
|---|---|---|---|
| 5,320,908 A * | 6/1994 | Sodervall et al. ............ | 428/461 |
| 5,395,651 A | 3/1995 | Sodervall et al. | |
| 5,747,178 A | 5/1998 | Sodervall et al. | |
| 5,965,204 A | 10/1999 | Sodervall et al. | |
| 6,093,414 A | 7/2000 | Capelli | |
| 6,224,983 B1 | 5/2001 | Sodervall et al. | |
| 7,435,773 B1 | 10/2008 | Nippa | |
| 8,784,928 B2 | 7/2014 | Terry et al. | |
| 2003/0026911 A1 | 2/2003 | Schall | |
| 2004/0208908 A1 * | 10/2004 | Modak ................. | A61K 31/155 424/423 |
| 2007/0237945 A1 | 10/2007 | Ohrlander et al. | |
| 2007/0237946 A1 | 10/2007 | Ohrlander et al. | |
| 2009/0123733 A1 | 5/2009 | Ohrlander et al. | |
| 2009/0319035 A1 | 12/2009 | Terry | |
| 2010/0028436 A1 | 2/2010 | Ohrlander et al. | |

FOREIGN PATENT DOCUMENTS

| | | |
|---|---|---|
| JP | 2002-535090 A | 10/2002 |
| JP | 2009-528855 A | 8/2009 |
| JP | 2009-533081 A | 9/2009 |

OTHER PUBLICATIONS

U.S. Appl. No. 13/383,535, filed Jan. 11, 2012 Non-Final Office Action dated Feb. 14, 2014.
AU 2011332884 filed Jun. 13, 2013 Notice of Acceptance dated Aug. 2, 2016.
IL 226535 filed May 23, 2013 Office Action dated Mar. 31, 2016.
JP 2013-541052 filed Jan. 18, 2012 First Office Action dated Oct. 13, 2015.

* cited by examiner

*Primary Examiner* — Dah-Wei D Yuan
*Assistant Examiner* — Andrew Bowman
(74) *Attorney, Agent, or Firm* — Rutan & Tucker, LLP

(57) ABSTRACT

Methods for the deposition of silver-comprising films on nonconducting substrates, and, more particularly, to deposition of such films that are very thin, are provided. The surface of nonconducting substrates is modified with a superabsorbent polymer to increase silver deposition when compared to a non-modified surface. Also provided are films produced using a swelling agent, whereby porosity of the surface of the nonconducting substrate is increased, thereby permitting increased silver deposition when compared to an unmodified surface.

15 Claims, No Drawings

DEPOSITION OF A SILVER LAYER ON A NONCONDUCTING SUBSTRATE

INCORPORATION BY REFERENCE TO RELATED APPLICATIONS

This application is a continuation of U.S. patent application Ser. No. 13/383,535, filed on Jan. 11, 2012, now U.S. Pat. No. 8,784,928, which is a U.S. national phase application under 35 U.S.C. §371 of International Application No. PCT/US2011/062086, filed Nov. 23, 2011, each of which is incorporated by reference herein in its entirety.

FIELD OF THE INVENTION

Methods for the deposition of silver-comprising films on nonconducting substrates, and, more particularly, to deposition of such films that are very thin, are provided. The surface of nonconducting substrates is modified with a superabsorbent polymer to increase silver deposition when compared to a non-modified surface. Also provided are films produced using a swelling agent, whereby porosity of the surface of the nonconducting substrate is increased, thereby permitting increased silver deposition when compared to an unmodified surface.

BACKGROUND OF THE INVENTION

Indwelling catheters are predominantly manufactured from natural and synthetic rubber latexes. They are made of nonconducting materials. Thin films of certain metals on nonconducting substrates can have important commercial applications. Thin films of conducting metals on transparent substrates are used in electronic display devices. Thin films can be used to reflect heat in solar shading or other solar devices, and to filter radiation from sunlight. A thin film can reduce the incidence of infection caused by a device that is introduced into the human body, when the film is coated onto the device before introduction into the body. Thin films are used in packaging as a vapor barrier coating. These applications are only illustrative of the thousands of uses of thin films, and are not limiting of their uses.

U.S. Pat. No. 6,224,983 to Sodervall et al., which is incorporated by reference herein in its entirety, teaches that metallic silver can be deposited upon the surface of a nonconducting substrate using a multi-step wet deposition process. The surface is cleaned, and then activated in an aqueous solution containing stannous ion. The silver is deposited as a colloidal material from an aqueous solution of a silver-containing salt, a reduction agent that reduces the salt to form the metallic silver, and a deposition control agent that prevents the silver from nucleating throughout the solution. After the substrate is coated, the coating is stabilized in an aqueous solution of a salt of a metal from the platinum group or gold, dissolved in dilute hydrochloric acid. The process is particularly effective for depositing uniform films of 2 to 2000 Angstroms thickness, which strongly adhere to the substrate.

U.S. Pat. No. 5,747,178 to Sodervall et al., which is incorporated by reference herein in its entirety, is directed to deposition of a silver layer on nonconducting substrates. U.S. Pat. No. 5,747,178 discloses a process for depositing thin, uniform layers of silver onto a wide variety of nonconducting substrates. The silver layer is disclosed as being adherent and effective in various uses, including, for example, antimicrobial medical applications, barrier packaging, and optical filters. The process can be performed at ambient temperature or, at most, slightly elevated temperature, using conventional industrial chemical procedures. U.S. Pat. No. 5,747,178 discloses that it is highly controllable and reproducible, producing virtually identical layers on large numbers of substrates, and that tests have shown that the yields of good quality coated parts using the approach are very high.

U.S. Pat. No. 5,747,178 discloses an approach to depositing a thin, uniform layer of silver, preferably 2 to 2000 Angstroms thick, at the rate of about 5-7 Angstroms per second in the deposition solution. U.S. Pat. No. 5,747,178 also discloses that the thickness of the surface layer is readily controlled, and that the resulting silver layer is adherent to the surface of the nonconducting substrate.

Other patents and patent publications including disclosures related to silver films on nonconducting substrates include U.S. Pat. No. 5,320,908; U.S. Pat. No. 5,395,651; U.S. Pat. No. 5,965,204; U.S. Patent Publication No. 2007/237945; U.S. Patent Publication No. 2007/237946; U.S. Patent Publication No. 2009/123733; U.S. Patent Publication No. 2010/028436; and U.S. Patent Publication No. 2011/236441, the contents of each of which are hereby incorporated herein by reference in their entireties.

SUMMARY OF THE INVENTION

A method for depositing silver films, or films of other metals, at acceptable levels, on nonconducting substrates is useful. By providing more uniform films, or films comprising more silver, or by promoting penetration of silver into a surface of a nonconducting device, especially a medical device, better clinical outcomes may be obtained due to the improved antibacterial properties of the device or a greater ability of the device to retain and/or deploy at least a portion of the deposited silver when in use.

Accordingly, in a first aspect, a method for preparing an antimicrobial medical device is provided, comprising: providing a nonconducting material; treating a surface of the nonconducting material by at least one of depositing a superabsorbent polymer on the surface or by exposing the surface to a swelling agent; depositing silver metal by exposing the treated surface to an aqueous solution of a silver salt in a presence of a deposition control agent; and treating the silver metal with a stabilizing amount of one or more metals selected from the group comprising platinum group metals and gold, whereby an adhesive, thin, uniform, transparent, antimicrobial, biocompatible coating comprising silver metal is obtained.

In an embodiment of the first aspect, treating the surface of the nonconducting material comprises depositing a superabsorbent polymer on the surface and exposing the surface to a swelling agent.

In an embodiment of the first aspect, depositing a superabsorbent polymer on the surface and exposing the surface to a swelling agent are conducted simultaneously.

In an embodiment of the first aspect, depositing a superabsorbent polymer on the surface and exposing the surface to a swelling agent are conducted sequentially.

In a second aspect, a method for preparing an antimicrobial medical device is provided, comprising: providing a nonconducting material; treating a surface of the nonconducting material by depositing a superabsorbent polymer on the surface; depositing silver metal by exposing the treated surface to an aqueous solution of a silver salt in a presence of a deposition control agent; and treating the silver metal with a stabilizing amount of one or more metals selected from the group comprising platinum group metals and gold, whereby an adhesive, thin, uniform, transparent, antimicrobial, biocompatible coating comprising silver metal is obtained.

In an embodiment of the second aspect, the superabsorbent polymer is deposited on the surface from an aqueous solution of a cross-linked $C_{10-30}$ alkyl acrylate copolymer.

In an embodiment of the second aspect, the aqueous solution of the cross-linked $C_{10-30}$ alkyl acrylate copolymer further comprises latex.

In an embodiment of the second aspect, the aqueous solution further comprises sodium chloride and potassium hydroxide.

In an embodiment of the second aspect, the aqueous solution comprises from about 0.1 to about 1.0 parts by weight sodium chloride, from about 0.05 to about 1.0 parts by weight of the superabsorbent polymer, from about 0.1 to about 10 parts by weight of potassium hydroxide, and from about 10 to about 50 parts by weight latex.

In a third aspect, a method for preparing an antimicrobial medical device is provided, comprising: providing a nonconducting material; treating a surface of the nonconducting material by exposing the surface to a swelling agent; depositing silver metal by exposing the treated surface to an aqueous solution of a silver salt in a presence of a deposition control agent; and treating the silver metal with a stabilizing amount of one or more metals selected from the group comprising platinum group metals and gold, whereby an adhesive, thin, uniform, transparent, antimicrobial, biocompatible coating comprising silver metal is obtained.

In an embodiment of the third aspect, the swelling agent is an alcohol and/or a water-miscible solvent.

In an embodiment of the third aspect, the alcohol is selected from the group comprising methanol, ethanol, isomers of propanol, isomers of butanol, isomers of pentanol, and combinations thereof.

In an embodiment of the third aspect, the water-miscible solvent is selected from the group comprising acetone, tetrahydrofuran, dimethylformamide, dimethlysulfoxide, acetonitrile, and combinations thereof.

In an embodiment of the third aspect, treating the surface and depositing silver metal are conducted simultaneously, wherein the swelling agent is included in the aqueous solution of a silver salt.

In an embodiment of the third aspect, treating the surface and depositing silver metal are conducted sequentially, wherein the swelling agent is included in a different solution from the aqueous solution of a silver salt.

In an embodiment of the third aspect, the swelling agent is included in a different solution from the aqueous solution of a silver salt, and wherein a same or different swelling agent is included in the aqueous solution of a silver salt.

In an embodiment of any one of the first through third aspects or embodiments thereof, the method further comprises activating the surface of the nonconducting material by exposing the surface to a base or to a compound configured to release chlorine. The base can be a hydroxide, e.g., sodium hydroxide or potassium hydroxide. The compound configured to release chlorine can be stannous chloride.

In an embodiment of any one of the first through third aspects or embodiments thereof, the nonconducting surface comprises latex, and the method further comprises activating the surface of the nonconducting material by exposing the surface to sodium hypochlorite.

In an embodiment of any one of the first through third aspects or embodiments thereof, the nonconducting surface comprises latex, and the method further comprises activating the surface of the nonconducting material by exposing the surface to an alcoholic base activation solution.

In an embodiment of any one of the first through third aspects or embodiments thereof, the method further comprises rinsing the silver coating in demineralized water and drying the coating.

In an embodiment of any one of the first through third aspects or embodiments thereof, the deposition control agent is selected from the group comprising sodium citrate, sodium acetate, sodium hydroxide, potassium hydroxide, ammonia, and combinations thereof.

In an embodiment of any one of the first through third aspects or embodiments thereof, the platinum group metal is platinum or palladium. The platinum group metal can be in combination with gold.

In an embodiment of any one of the first through third aspects or embodiments thereof, depositing is conducted in the absence of a reducing agent.

In an embodiment of any one of the first through third aspects or embodiments thereof, the nonconducting substrate is latex.

In an embodiment of any one of the first through third aspects or embodiments thereof, the nonconducting substrate is silicone.

In an embodiment of any one of the first through third aspects or embodiments thereof, wherein the antimicrobial medical device is a Foley catheter.

In a fourth aspect, an antimicrobial medical device is provided, prepared according to any of the aforementioned aspects or embodiments.

In an embodiment of the fourth aspect, a topmost layer of the device comprises adsorbed silver.

In a fifth aspect, an antimicrobial medical device is provided, prepared according to any of the first or second aspects or their embodiments, wherein the topmost layer comprises a superabsorbent polymer.

In a sixth aspect, an antimicrobial medical device is provided, prepared according to any of the first or third aspects or their embodiments, the topmost layer comprises a porous layer of silicone or latex.

In an embodiment of the sixth aspect, the porous layer is formed via exposure to a swelling agent.

In a seventh aspect, an antimicrobial medical device is provided, the device comprising a topmost layer comprising a cross-linked $C_{10-30}$ alkyl acrylate copolymer with silver incorporated therein and thereupon.

In an embodiment of the seventh aspect, the device further comprises a latex layer beneath the topmost layer.

In an embodiment of the seventh aspect, the device is a Foley catheter.

In an eighth aspect, an antimicrobial medical device is provided, the device comprising a topmost porous layer, the topmost porous layer comprising a nonconducting material selected from the group comprising silicone and latex, the topmost layer having silver deposited within its pores.

In an embodiment of the eighth aspect, the device further comprises a latex layer beneath the topmost layer.

In an embodiment of the eighth aspect, the device is a Foley catheter.

In a ninth aspect, a coating for an antimicrobial medical device is provided, comprising a cross-linked $C_{10-30}$ alkyl acrylate copolymer with silver incorporated therein and thereupon.

In a tenth aspect, a coating for an antimicrobial medical device is provided, the coating comprising porous silicone or porous latex having silver deposited within the pores.

DETAILED DESCRIPTION OF VARIOUS EMBODIMENTS

In exemplary embodiments, the surface of nonconducting substrates is modified with a superabsorbent polymer to increase silver deposition over that observed for a non-modified surface. The superabsorbent modified layer is adherent to the outermost layer of a Foley catheter. The deposition of silver is greatly enhanced compared to the surface without the superabsorbent modification. The modified surface swells during the silver deposition process, opening pore sites to anchor the silver deposition. The silver deposition is increased by an increase in the concentration of superabsorbent polymers in the outermost layer of latex dipping. A nonconducting substrate for silver deposition in a more effective and controlled manner is provided. Nonconducting substrates are difficult to deposit a uniform layer of silver. The methods of exemplary embodiments can increase the number of sites able to accept uniform deposition of silver. Therefore, the silver amount on the nonconducting substrates of, e.g., catheters can be increased. The substrates can be natural rubber, synthetic polyisoprene, nitrile rubber, chloroprene, styrene-butadiene copolymer, etc.

Metal Ion Solutions

In exemplary embodiments, a nonconducting substrate is provided with a film of metal particles, such as silver particles. The term "metal" or "metallic" as used herein are broad terms, and are to be given their ordinary and customary meaning to a person of ordinary skill in the art (and are not to be limited to a special or customized meaning), and refer without limitation to pure metals, mixtures of two or more metals, mixtures of metals and non-metals, metal oxides, metal alloys (e.g., copper-silver allows, silver-manganese alloys, iron-copper alloys, chromium-silver alloys, gold-silver alloys, and magnesium-silver alloys), mixtures or combinations of any of the aforementioned materials, and other substances containing at least one metal. Suitable metals include the transition metals (e.g., Group VI to Group XI metals), metals in the main group, and their oxides. In addition to silver, metals that can be advantageously deposited by the methods of exemplary embodiments include, but are not limited to, platinum group metals (e.g., platinum, palladium, rhodium, iridium, ruthenium, and osmium) or gold, as well as other transition metals (e.g., Mg, Ni, Cu, Zn, Fe, and the like). The metal can be provided in sub-micrometer sized particles, e.g., nanoparticles or Angstrom-scale particles; however, in certain embodiments larger particles or other forms may also be employed. Many transition and main group metal oxides are can be applied, for example, AgO, or other oxides such as iron oxide and zinc oxide. While certain embodiments are described in relation to deposition of silver, it is understood that other metals can be deposited using similar methods, as will be appreciated by one of skill in the art.

A single metal or metal oxide may be employed, or a combination of two or more metals or metal oxides may be employed. The combination may include a mixture of particles each having different metal or metal oxide compositions. Alternatively, the particles themselves may contain more than one metal or metal oxide. Suitable particles may include alloys of two or more different kinds of metals, or mixtures or alloys of metals and nonmetals. Suitable particles may also include particles having a metal core with a layer of the corresponding metal oxide making up the surface of the particle. The metallic particles may also include metal or metal oxide particles on a suitable support material, for example, a silica or alumina support. Alternatively, the metallic particles may include particles including a core of support material substantially encompassed by a layer of catalytically active metal or metal oxide. In addition to the above-mentioned configurations, the metallic particles may in any other suitable form.

The particles may be prepared by any suitable method as is known in the art. When preparing metallic particles, suitable methods include, but are not limited to, wire electrical explosion, high energy ball milling, plasma methods, evaporation and condensation methods, and the like. However, in exemplary embodiments, the particles are prepared via reduction of metal ions in solution, as described below. Alternatively, when silver metal is employed, colloidal silver products as are commercially available can be employed, e.g., those sold by Solutions IE, Inc. under the trade names CS Plus and CS Ultra. Other colloidal silver products that can be used as the silver source include ASAP, Sovereign Silver, Silver Max, and the like.

The particles of exemplary embodiments can have an average particle size of atomic dimensions (as little as one atom) up to 1, 2, 3, 4, 5, 6, 7, 8, 9, 10, 50, 100, 150, 200, 250, 300, 350, 400, 500, or 1000 nm or greater. In exemplary embodiments, the particles are of a substantially uniform size distribution, that is, a majority of the metallic particles present have a diameter generally within about ±50% or less of the average diameter, e.g., within about ±45%, 40%, 35%, 30% or less of the average diameter, e.g., within ±25% or less of the average diameter, e.g., within ±20% or less of the average diameter. The term "average" includes both the mean and the mode.

While a uniform size distribution may be employed, individual particles having diameters above or below the specified range may be present, and may even constitute the majority of the particles present, provided that a substantial amount of particles having diameters in the specified range are present. In other embodiments, it may be desirable that the particles constitute a mixture of two or more particle size distributions, for example, a portion of the mixture may include a distribution on nanometer-sized particles, and a portion of the mixture may include a distribution of micron-sized particles. The particles of exemplary embodiments may have different forms. For example, a particle may constitute a single, integrated particle not adhered to or physically or chemically attached to another particle. Alternatively, a particle may constitute two or more agglomerated or clustered smaller particles that are held together by physical or chemical attractions or bonds to form a single larger particle. The particles may have different atomic level structures, including but not limited to, for example, crystalline, amorphous, and combinations thereof. In various embodiments, different combinations of particles having various properties can be included, including, but not limited to, particle size, shape or structure, chemical composition, crystallinity, and the like.

The particles can be deposited in a thin, uniform layer, e.g., from about 2 Å to about 2000 Å or more angstroms in thickness, e.g., a monolayer or less, or multiple atomic layers, up to micron thickness. In alternative embodiments, the particles can be deposited in a non-uniform layer (e.g., as islands or aggregates, isolated and/or in contact with adjacent islands or aggregates). While particular film thicknesses are discussed herein, alternatively, the films can be described in terms of weight of silver deposited per unit of substrate surface area.

Any suitable method can be employed for applying the metal to the nonconducting substrate. The substrate is advantageously subjected to a process for increasing deposition of silver or other metal, as described herein. This process can include swelling of the substrate surface and/or application of a superabsorbent polymer. As discussed above, the metal is deposited onto the nonconducting substrate from a solution of metal salt(s). Aqueous solutions can be employed. Optionally, the metal salt solution can include one or more swelling agents, as discussed herein. The nonconducting substrate can optionally be subjected to separate swelling treatment or optionally be provided with a superabsorbent polymer as described herein. The substrate, after the optional swelling and/or superabsorbent polymer treatment steps, is then exposed to the solution, e.g., by dipping, spraying, or other methods of application. The silver deposition solution can be freshly prepared, e.g., less than about four hours prior to use, and can have a pH of 8 or higher; however, solutions prepared more than 4 hours prior to use, or having pH of less than 8 can also be employed in certain embodiments. A fresh deposition solution can be prepared after multiple uses, as the quality of the deposited film can be reduced under certain circumstances if the solution is used too many times. The solution includes a silver-containing salt, e.g., silver nitrate ($AgNO_3$), in an effective amount, e.g., from about 0.01 grams per liter or less to about 0.2 grams per liter or more, e.g., from about 0.015 grams per liter to about 0.02, 0.03, 0.04, 0.05, 0.6, 0.07, 0.08, 0.1, 0.11, 0.12, 0.13, 0.14, 0.15, 0.16, 0.17, 0.18, or 0.19 grams per liter. If the silver content is above about 0.10 grams per liter, the elemental silver may form non-uniformly, in the solution or on the container walls, whereas if the silver content is below an effective amount, there is insufficient silver to form a film in the specified time. Aqueous solutions can be employed; however, co-solvents and other liquids can also be employed, e.g., alcohols or water-miscible solvents, which for certain substrates can confer the benefit of subjecting the surface to swelling. Suitable alcohols include aliphatic alcohols and other carbon-containing alcohols, having, e.g., from 1 to 24 carbon atoms. In addition to aliphatic alcohols, alicyclic alcohols, aromatic alcohols, unsaturated alcohols, as well as substituted aliphatic, alicyclic, aromatic, and unsaturated alcohols, etc. can be employed. Alcohols that can be employed include $C_{1-5}$ alcohols such as methanol, ethanol, propanol, isopropanol, butanols, and pentanols. Monohydric, dihydric, or polyhydric alcohols can be suitable for use. Water miscible solvents include, but are not limited to, acetone, tetrahydrofuran (THF), dimethylformamide (DMF), dimethlysulfoxide (DMSO), and acetonitrile.

The deposition solution can contain a reduction agent present in sufficient amount to reduce the silver-containing salt to elemental silver. Suitable reduction agents include formaldehyde, hydrazine sulfate, hydrazine hydroxide, and hypophosphoric acid, the reducing sugars, organic aldehydes, hydroxyl-containing aldehydes, glucose, mannose, galactose, xylose, ribose, and arabinose. Other reducing sugars containing hemiacetal or keto groupings may be employed, for example, maltose, sucrose, lactose, fructose, and sorbose. Pure sugars may be employed, but crude sugars and syrups such as honey, corn syrup, invert syrup or sugar, and the like may also be employed. Other reducing agents include alcohols, e.g., polyhydric alcohols, such as glycerol, sorbitol, glycols, especially ethylene glycol and propylene glycol, and polyglycols such as polyethylene and polypropylene glycols. In alternative embodiments, other reducing agents can be used, such as carbon monoxide, hydrogen, or ethylene. The reducing agent can be present in an amount of about 0.0005 milliliters per liter of solution to about 0.01 milliliters per liter of solution or more, e.g., about 0.001 milliliters per liter of solution. Too large a concentration of the reduction agent may cause deposition of silver throughout the solution and on the container walls, while too small a concentration may result in an insufficient formation of metallic silver on the substrate.

In certain embodiments, a deposition control agent can advantageously be employed in the solution in an amount sufficient to slow the deposition reaction to prevent the reduced metallic silver from precipitating directly from solution as a fine metallic powder, or precipitating onto the walls of the container. Deposition control agents include inverted sugar, also known as invertose, succinic acid, sodium citrate, sodium acetate, sodium hydroxide, potassium hydroxide, and ammonia. The deposition control agent can be present in an amount of from about 0.01 grams per liter of solution or less to about 0.1 grams per liter of solution or more, e.g., about 0.05 grams per liter of solution. If too little is present, the above-described precipitation from solution of metallic silver particles may occur, while if too much is present, the silver-containing salt may become too stable for precipitation onto the nonconducting substrate.

The concentrations of the reduction agent and the deposition control agent can be adjusted to achieve the specified results, depending upon the substrate material, the metal, the thickness of the film, the conditions of deposition, and the concentration of metal, e.g., silver in the solution. For example, for thin films the silver salt concentration can be relatively low, along with the concentrations of the reduction agent and the deposition control agent.

In preparing the deposition solution, each of the components of the solution can be individually dissolved in demineralized water or other suitable solvent; however, it can be advantageously to add various components simultaneously, and/or in any sequence. The various pre-solutions containing the individual components are then mixed, and optionally diluted, in suitable amounts to achieve the concentrations indicated previously. Mixing the components together during the solution-forming stage may result in instability and precipitation of silver prematurely. If the solution is to be stored before use, it can be stored in darkness to prevent premature deposition.

The silver salt that is the source of the deposited silver can be sensitive to decomposition by light in the visible range, and such light can therefore be excluded from the deposition procedure. The combination of silver salt and reduction agent, used in darkness, permits the silver to be reduced from the salt in a colloidal state to be deposited upon the surface of the substrate. This colloidal state is particularly beneficial to achieve good adhesion of the completed silver film to the substrate surface, good transparency as a thin film, biocompatibility, tissue friendliness, and non-toxicity. One or more of these various properties may be applicable in different uses of the thin film. Good adhesion is a characteristic in nearly all uses. Biocompatibility, tissue friendliness, and non-toxicity are characteristics in medical applications. Uniform transparency is a characteristic for electrical instrument requirements.

The substrate surface is exposed to the deposition solution by any appropriate procedure. Dipping into the solution can be performed, but the solution may be applied by any convenient technique such as spraying or brushing. The silver film deposits uniformly from the solution at a rate that may be controlled by the concentration of the silver salt. With a concentration of about 0.015 grams per liter of silver nitrate, the deposition rate is about 5 Angstroms per second at ambient temperature (e.g., 20-25° C.); although in some circumstances the rate may be as high as about 7 Angstroms per second at ambient temperature, with the deposition rate increasing with increasing temperature. If a thin film is specified, the temperature of deposition is maintained sufficiently low such that deposition is controllably slow. Thus, a repeatable, uniform thin film about 50 Angstroms thick can be prepared by immersion for, e.g., 10 seconds. Increasing the deposition time increases the film thickness proportionately, at least up to thicknesses of about 2000 Angstroms. This relationship between deposition time and film thickness is presented as a guideline, and an actual calibration can be readily obtained for any particular combination of substrate and treatment procedures. After deposition is complete, the coated substrate is removed from the deposition solution and rinsed in demineralized water or other suitable rinsing solution, and allowed to dry by evaporation (e.g., optionally with assistance by elevated temperature, vacuum, and/or circulation of air or other gas(es)).

While relatively thin films can be used in certain embodiments, in other embodiments, film thicknesses greater than 2000 Angstroms can be deposited, e.g., 2500 Angstroms, 3000 Angstroms, 3500 Angstroms, 4000 Angstroms, 4500 Angstroms, or 5000 Angstroms or more, according to the methods of exemplary embodiments. Because the silver is deposited in pores of a top layer of the material (e.g., in the case of a top layer subjected to exposure to a swelling agent), or is incorporated by adsorption into a top layer (e.g., a superabsorbent polymer), larger amounts of silver can penetrate into or be incorporated by the antimicrobial coating than by conventional methods. Because larger amounts of silver are incorporated into the coating, more antimicrobial silver is available for release when used in a clinical setting, e.g., a Foley catheter that is positioned within a patient. Greater antibacterial activity and/or longer duration of antibacterial activity can be observed for surfaces treated according to methods of exemplary embodiments.

Upon deposition, the silver is present as a metallic deposit upon the surface of the nonconducting substrate. It can be used in this condition for some applications, but in certain embodiments can be stabilized to avoid chemical and physical changes during use. The metallic silver deposit can be stabilized by exposing the surface to a stabilization solution. This solution can be prepared by dissolving at least about 0.001, e.g., from about 0.001 to about 0.1, e.g., from about 0.02 to about 0.05, grams per liter of a salt of a platinum group metal (such as platinum, palladium, rhodium, iridium, ruthenium, or osmium) or gold, e.g., a platinum salt, into dilute hydrochloric acid or other acidic solution. The dilute acid can be prepared by boiling conventional concentrated hydrochloric acid to remove water, and then diluting the acid with demineralized water to a pH of from about 3.0 to about 4.8. The stabilization solution can be used within 8 hours of preparation, and can be discarded after 2-3 uses; however, older or more frequently used solutions can also be suitable for use. The stabilization solution is contacted to the surface for at least about 5 seconds at ambient temperature and for 1-20 minutes at ambient temperature. After the stabilization treatment, the substrate surface is rinsed in demineralized water or another suitable rinsing solution and dried. It is then ready for use, having an adherent silver coating that is uniformly of a thickness determined by the deposition time. Large numbers of pieces can be coated at a time using this approach, and the pieces may be of irregular size and shape. Coating is accomplished on the inside of even small bores or porous substrates if the solutions can be contacted to the inside walls. In some instances, the various solutions can be forced through the small bores to achieve wetting and reaction. Using the techniques of the exemplary embodiments, silver can be coated into bores of about 0.002 millimeters in diameter or smaller.

The preceding processing treatment is sensitive to impurities in the solutions, such that reagent grade chemicals and demineralized (deionized) water can be used.

Nonconducting Substrates Treated with Superabsorbent Polymers

Any suitable nonconducting substrate (or conducting substrate provided with a nonconducting coating) can be employed in the methods of exemplary embodiments. In certain embodiments, the nonconducting substrate is provided with a superabsorbent polymer coating.

The term "superabsorbent polymer" as used herein is a broad term, and is to be given its ordinary and customary meaning to a person of ordinary skill in the art (and is not to be limited to a special or customized meaning), and refers without limitation to a polymer that absorbs a minimum of 20 times its own weight in water or another liquid. The polymer can retain its identity and have sufficient physical strength to resist flow and fusion with neighboring particles, and to swell but not dissolve. Water absorbing polymers, which are classified as hydrogels when crosslinked, absorb aqueous solutions through hydrogen bonding with water molecules. A superabsorbent polymer's ability to absorb water is a factor of the ionic concentration of the aqueous solution. In deionized and distilled water, a superabsorbent polymer may absorb as much as 500 times its weight (from 30-60 times its own volume), but when put into a 0.9% saline solution, the absorbency may drop to 50 times its weight. The presence of valence cations in the solution may impede the polymer's ability to bond with the water molecule.

Suitable superabsorbent materials may be selected from natural, biodegradable, synthetic, and modified natural polymers and materials. In addition, the superabsorbent material may comprise inorganic materials, such as silica gels, or organic compounds such as crosslinked polymers. The term "crosslinked" used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. The total absorbency and swelling capacity are controlled by the type and degree of cross-linkers used to make the gel. Low density cross-linked superabsorbent polymers generally have a higher absorbent capacity and swell to a larger degree. These types of superabsorbent polymers also have a softer and stickier gel formation. High cross-link density polymers exhibit lower absorbent capacity and swell, but the gel strength is firmer and can maintain particle shape even under modest pressure.

Hydrophilic gels that are usually referred to as hydrogels are networks of polymer chains that are sometimes found as colloidal gels in which water is the dispersion medium. Hydrogels typically exhibit the ability to swell in water and retain a significant fraction (>20%) of water within their structure, without dissolving in water.

The mechanisms by which superabsorbent polymers absorb liquid may include reversible changes of their crystal structure (e.g., silica gel and anhydrous inorganic salts), physical entrapment of water via capillary forces in their macro-porous structure (e.g., soft polyurethane sponge), a combination of the aforementioned mechanisms and hydration of functional groups, and dissolution and thermodynamically favored expansion of the macromolecular chains limited by cross-linkages.

Superabsorbent polymer materials are organic materials with enormous capability of water absorption. Superabsorbent polymers as hydrogels, relative to their own mass can absorb and retain extraordinary large amounts of water or aqueous solution. These ultrahigh absorbing materials can imbibe deionized water as high as 1,000-100,000% (10-1000 g/g) whereas the absorption capacity of common hydrogels is not more than 100% (1 g/g). Commercial superabsorbent polymer hydrogels are generally sugar-like hygroscopic materials with white-light yellow color. The superabsorbent polymer particle shape (granule, fiber, film, etc.) is typically preserved after water absorption and swelling, i.e., the swollen gel strength should be high enough to prevent a loosened state. This is a major practical feature that contrasts superabsorbent polymers from other hydrogels. Hydrogels and superabsorbent polymers that may be suitable for use in exemplary embodiments are described in the following articles: Zohuriaan-Mehr et al. "Superabsorbent Polymer Materials: A Review" Several papers have been published to review, Iranian Polymer Journal 17 (6), 2008, 451-477; Mathur A M, Moorjani S K, Scranton A B, Methods for synthesis of hydrogel networks: A review, J Macromol Sci-Rev Macromol Chem Phys, C36, 405-430, 1996; Kulicke W-M, Nottelmann H, Structure and swelling of some synthetic, semisynthetic, and biopolymer hydrogels, Adv Chem Ser, 223, 15-44, 1989; Kazanskii K S, Dubrovskii S A, Chemistry and physics of "agricultural" hydrogels, Adv Polym Sci, 104, 97-140, 1992; Bouranis D L, Theodoropoulos A G, Drossopoulos J B, Designing synthetic polymers as soil conditioners, Commun Soil Sci Plant Anal, 26, 1455-1480, 1995; Dutkiewicz J K, Superabsorbent materials from shellfish waste-A review, J Biomed Mater (Appl Biomater), 63, 373-381, 2002; Ichikawa T, Nakajima T, Superabsorptive Polymers (from natural polysaccharides and polypeptides), In: Polymeric Materials Encyclopedia, Salamone (Ed), CRC, Boca Raton (Fla.), 8051-8059, 1996; Athawale V D, Lele V, Recent trends in hydrogels based on starch-graft-acrylic acid: A review, Starch/Starke, 3, 7-13, 2001; Buchholz F L, Recent advances in superabsorbent polyacrylates, Trend Polym Sci, 2, 277-281, 1994; Chin Y-R, Al-Dayel A, Acrylic acid based superabsorbent polymer, Process Economics Program Review No. 85-1-2, Stanford Research Institute, SRI International, December 1985; Chatterjee P K, Gupta B S (Eds), Absorbent Technology, Elsevier, Amsterdam, ch 1-2, 2002; Buchholz F L, Graham A T, Modern Superabsorbent Polymer Technology, Wiley-VCH, New York, Ch 1-7, 1998; Brannon-Peppas L, Harland R S, Absorbent Polymer Technology, Elsevier, Amsterdam, Ch 1-4, 1990; and Po R, Water-absorbent polymers: A patent survey, J. Macromol. Sci-Rev Macromol Chem Phys, C34, 607-662, 1994. The solution and suspension polymerization techniques used for preparing the acrylate superabsorbents have been discussed in detail in Dayal U, Mehta S K, Choudhari M S, Jain R, Synthesis of acrylic superabsorbents, J Macromol Sci-Rev Macromol Chem Phys, C39, 507-525, 1999.

Superabsorbent polymers may be categorized to four groups on the basis of presence or absence of electrical charge located in the crosslinked chains: non-ionic; ionic (including anionic and cationic); amphoteric electrolyte (ampholyte) containing both acidic and basic groups; and zwitterionic molecules (e.g. polybetaines) containing both anionic and cationic groups in each structural repeating unit. The majority of commercial superabsorbent polymer hydrogels are anionic. Superabsorbent polymers are also classified based on the type of monomeric unit used in their chemical structure, thus conventional superabsorbent polymers include cross-linked polyvinyl alcohol, polyvinyl pyrrolidone, polyacrylates and polyacrylamides; hydrolyzed cellulose-polyacrylonitrile (PAN or starch-PAN graft copolymers; and cross-linked copolymers of maleic anhydride.

Superabsorbent polymers include synthetic (petrochemical-based) and natural. The latter can be divided into two main groups, i.e., the hydrogels based on polysaccharides and others based on polypeptides (proteins). The natural-based superabsorbent polymers are usually prepared through addition of some synthetic parts onto the natural substrates, e.g., graft copolymerization of vinyl monomers on polysaccharides. A variety of monomers, mostly acrylics, are employed to prepare superabsorbent polymers. Acrylic acid (AA) and its sodium or potassium salts, and acrylamide (AM) are most often used in the industrial production of superabsorbent polymers. Other monomers such as methacrylic acid (MAA), methacrylamide (MAM), acrylonitrile (AN), 2-hydroxyethylmethacrylate (HEMA), 2-acrylamido-2-methylpropane sulfonic acid (APMS), N-vinyl pyrrolidone (NVP), vinyl sulfonic acid (VSA) and vinyl acetate (VAc) are also used. In the modified natural-based superabsorbent polymers (i.e., hybrid superabsorbents) trunk biopolymers such as cellulose, starch, chitosan, gelatin and some of their possible derivatives e.g., carboxymethyl cellulose (CMC) are also used as the modifying substrate.

The bifunctional compound N,N'-methylene bisacrylamide (MBA) is most often used as a water soluble cross-linking agent. Ethyleneglycol dimethacrylate (EGDMA), 1,1,1-trimethylolpropane triacrylate (TMPTA), and tetraalyloxy ethane (TAOE) are known examples of two-, three- and four-functional cross-linkers, respectively.

Superabsorbent polymers of petrochemical origin are typically produced from the acrylic monomers, most frequently acrylic acid (AA), its salts, and acrylamide (AM). Carbohydrate polymers (polysaccharides) are the cheapest and most abundant, available, and renewable organic materials. Chitin, cellulose, starch, and natural gums (such as xanthan, guar, and alginates) are some of the most important polysaccharides. Generally, the reported reactions for preparing the polysaccharide-based superabsorbent polymers are held in two main groups; (a) graft copolymerization of suitable vinyl monomer(s) on polysaccharide in the presence of a cross-linker, and (b) direct cross-linking of polysaccharide. The earliest commercial superabsorbent polymers were produced from starch and AN monomer by employing a cross-linker.

Superabsorbent polymer hydrogels comprising polypeptides as the main or part of their structure can be derived from soybean, fish, and collagen-based proteins. Proteins can also be modified by either polysaccharides or synthetics to produce hybrid hydrogels with super-swelling properties.

Collagen-based proteins including gelatin and hydrolyzed collagen (H-collagen; very low molecular weight products of collagen hydrolysis) have been used for preparing superabsorbent polymer materials. Homo-poly(amino acid)s of poly(aspartic acid)s, poly(L-lysine) and poly(-glutamic acid)s have also been employed to prepare superabsorbent polymer materials.

The superabsorbent polymer can be provided in the form of a solution, dispersion, or suspension in an appropriate solvent or other carrier, e.g., liquid. Depending upon the superabsorbent polymer employed, solubility, as evidenced by a clear gel, can be obtained by adjusting a pH of the solution. While mixing, an amount of compounded latex or other polymeric material having adhesive properties can be gradually added to the superabsorbent polymer-containing liquid to form a homogeneous solution or suspension. The process enhances the amount of silver deposition.

A substrate (conducting or nonconducting) can be dipped, sprayed, brushed, or otherwise applied with a solution, dispersion, or suspension of the superabsorbent polymer, optionally including latex or other adhesive material. Alternatively, a mold (e.g., for a glove, ventilator bellow, balloon, dental dam, condom or the like) or a substrate (e.g., a urinary catheter, vial, bottle, or the like) can be dipped in a nonconducting latex solution or dispersion one or more times to build up layers of latex to a specified thickness, a coagulant applied, and the applied layer allowed to dry. After the latex layer is built up to the specified thickness on the mold or substrate, a solution, dispersion, or suspension of the superabsorbent polymer, optionally including latex or other adhesive, is applied. One or more layers can be applied, after which the dipped substrate is dried (optionally with assist of elevated temperature, circulating air or other gas, and reduced humidity).

A coagulant dipping process is typically used to produce elastomeric articles from synthetic nonconducting substrate latex or other polymeric substrates, as are known in the art (e.g., natural rubber, polyisoprene, polychloroprene, nitrile, latex, nitrile latex, polystyrene-butadiene copolymer, etc.). Coagulant can be applied after the latex layers have been applied to a substrate to set the latex as described above, or the coagulant can be first applied to a mold, form or other substrate and dried before the substrate is dipped into a latex to produce a thicker layer of latex on the substrate.

The substrate thus prepared is then subjected to deposition of silver by the methods described herein. Use of the superabsorbent polymer increases the amount of silver or other metal that can be deposited by the deposition methods (e.g., deposition from metal salt solution) described herein.

Nonconducting Substrates Subjected to Swelling

In addition to, or as an alternative to treating a substrate with a superabsorbent polymer so as to improve silver or other metal deposition, the substrate utilizes a surface that exhibits swelling when contacted with an aqueous solution containing an oxidizing/activating agent and/or alcohol or other water-miscible solvent which swells the surface of the article. By first subjecting the surface to swelling, the amount of silver or other metal that can be deposited by the deposition methods (e.g., deposition from metal salt solution) described herein is increased. The oxidizing agent(s) or activating agent(s), if used, can be applied in a separate solution as a pretreatment, followed by application of the swelling agent(s) in a separate solution, or in a single step as one solution containing both the oxidizing/activating agent(s) and the swelling agent. Suitable substrate materials include any nonconducting material, such as, but not limited to, latex or silicone, that is capable of being swollen by alcohol or other water-miscible solvent. Thus, the surface can comprise latex or silicone (e.g., one or more conducting or nonconducting substrate materials), or the article can be formed entirely of latex or silicone. Moreover, the surface can be formed partially or entirely of the material capable of being swollen by alcohol or other water-miscible solvent. While not wishing to be bound by theory, the use of alcohol or water miscible solvent swelling agents results in swelling of and/or pore formation in the substrate surface, providing greater absorption of silver metal.

Suitable swelling agents include alcohols and water-miscible solvents. The alcohol can comprise, for example, and without limitation, methanol, ethanol, propanol, isopropanol, butanol, or combinations thereof. The water-miscible solvent can comprise, for example, and without limitation, acetone, tetrahydrofuran (THF), dimethylformamide (DMF), dimethylsulfoxide (DMSO), acetonitrile, and combinations thereof. Aqueous solutions containing one or more alcohols, one or more water-miscible solvents, and combinations thereof can advantageously be employed.

The oxidizing agent can be any compound or compounds that can clean and activate by oxidation. The substrate, such as a latex substrate, can be activated by a cleaning pretreatment with an alcohol/base or an alcohol/chlorine mixture. Additionally, a substrate, such as a silicone substrate, can be cleaned and activated by pretreating with an alcoholic base, such as methanolic potassium hydroxide. Further, the penetration of the activation treatment into the substrate can be improved by the addition of alcohol or water-miscible solvents to the bath. Certain activation salts, for example, stannous chloride, are advantageously soluble in alcohol. An aqueous solution containing stannous ion, e.g., a containing from 0.1-0.5 grams per liter of stannous chloride, can be advantageously used. For example, the oxidizing agent can be, for example, and without limitation chlorine and/or any compound that is capable of releasing chlorine in the aqueous solution, or at least one hydroxide, such as sodium hydroxide or potassium hydroxide. For example, chlorine can be used with latex, and hydroxide can be used with silicone. While an oxidizing agent can be employed, in certain embodiments it may be possible to prepare a suitably swelled surface without using an oxidizing agent. For certain nonconducting surfaces, e.g., latex surfaces, sodium hypochlorite and/or alcoholic base activation solutions can be advantageously employed to activate the surface.

In certain embodiments, the substrate, such as a latex substrate, can be activated by pretreatment with an alcohol or an alcohol/chlorine mixture. Alternatively, a substrate, such as a silicone substrate, can be activated by pretreating with alcohol, such as methanol, or an alcoholic base, such as methanolic potassium hydroxide. The alcohol component, such as alcohol or alcohol containing an oxidizing agent, can also be included in the aqueous solution of at least one metal salt. Thus, there can be pretreatment of the activated surface with the alcohol component and/or the alcohol component can be included in the aqueous deposition solution of at least one metal salt.

The swelling agent can be applied to a suitable substrate in a pretreatment step and/or the swelling agent can be included in the deposition solution of silver or other metal, cleaning solutions, rinsing solutions, or the like. The inclusion of alcohol or other water-miscible solvent into one or more of the solutions swells the top layer of the substrate, such as the surface of the article, and allows for greater adsorption or penetration of treatment chemicals which produces higher quantities of deposited metal (e.g., silver). Silver nitrate is soluble in aqueous organic solvents such as alcohol and THF, making these solvents particularly suited for use in silver deposition processes.

The methods of exemplary embodiments can be used in the manufacture of a Foley catheter that is positioned within a patient. Advantageous results according to the present exemplary embodiments include better clinical efficiency associated with the improved antibacterial properties of the device so prepared.

Additional cleaning steps, rinsing steps, drying steps, and/or disinfection steps can be conducted as part of the methods of exemplary embodiments, as will be appreciated by one of skill in the art.

Example 1

Carbopol® Ultrez 21 Polymer, a superabsorbent polymer available from Lubrizol Corp., Wickliffe, Ohio, is a self wetting crosslinked polyacrylic acid polymer that is synthesized in a cosolvent ethyl acetate/cyclohexane mixture. The cross-linked $C_{10-30}$ alkyl acrylate copolymer is dispersed in water with sodium chloride, and then adjusted to pH above 7.5 to produce a clear gel. While mixing, an amount of compounded latex is gradually added in to form a homogeneous solution. Other superabsorbent polymers such as Carbopol® 934 (a cross-linked polyacrylate polymer), Carbopol® 940 (a cross-linked polyacrylate polymer), and Carbopol® 980 (a cross-linked polyacrylate polymer) from Lubrizol Corp., Wickliffe, Ohio and Aqua Keep® SA605, Aqua Keep® SA60SXIII, Aqua Keep® SA55SXII, and Aqua Keep® AB60SXII (each composed mainly of sodium polyacrylate) from Sumitomo Seika Chemical Co., Ltd., Osaka, Japan are also suitable for the application to modify the topmost surface of the nonconducting substrate of a catheter.

A mold is dipped in a nonconducting latex solution or dispersion. A coagulant is applied and the dipped layer is allowed to air dry. After the latex layer is built up to the specified thickness, the mold is dipped in a solution, dispersion, or suspension of a superabsorbent polymer, including latex. One or more layers are applied, after which the dipped substrate is dried in an air circulating over for 30 minutes at 55° C., then for 45 minutes at 85° C. The mold is removed from the oven, cooled and the deposited layers are stripped from the mold.

A coagulant can optionally be employed. The coagulant can contain, e.g., 40 g calcium nitrate, 8 g calcium carbonate, and 52 g water. The mold is dipped in the coagulant, air dried, and then dwelled in compounded polyisoprene latex for 1-7 minutes, e.g., 2-5 minutes. After dipping, the gel film is dipped in the superabsorbent modified solution and then leached in water for 5 minutes, and dried in an air-circulated oven for 30 minutes at 55° C., and finally dried in an air-circulated oven for 45 minutes at 85° C.

The latex article thus prepared is then contacted with a silver solution or other metal solution by methods as described herein so as to deposit a layer of silver. In certain embodiments, treatment of the article with a superabsorbent polymer with latex prior as an optional step prior to silver deposition can enhance the amount of silver deposition on the article. Solutions of superabsorbent polymer with latex comprise (in parts by weight) the components as set forth in Tables 1 through 4.

TABLE 1

| Materials | Parts (Dry) | Parts (Wet) |
| --- | --- | --- |
| Deionized water | — | 70.91 |
| Sodium chloride | 0.3 | 0.3 |
| Modified Ultrez 21 - modified acrylic polymer, Ultrez 21, Lubrizol | 0.6 | 0.6 |
| Potassium hydroxide | 0.4 | 4.0 |
| Compounded synthetic latex | 15 | 24.19 |

TABLE 2

| Materials | Parts (Dry) | Parts (Wet) |
| --- | --- | --- |
| Deionized water | — | 74.36 |
| Sodium chloride | 0.3 | 0.3 |
| Modified acrylic polymer, Ultrez 21, Lubrizol | 0.15 | 0.15 |
| Potassium hydroxide | 0.1 | 1.0 |
| Compounded synthetic latex | 15 | 24.19 |

TABLE 3

| Materials | Parts (Dry) | Parts (Wet) |
| --- | --- | --- |
| Deionized water | — | 72.11 |
| Sodium chloride | 0.3 | 0.3 |
| Modified acrylic polymer, Ultrez 21, Lubrizol | 0.4 | 0.4 |
| Potassium hydroxide | 0.3 | 3.0 |
| Compounded synthetic latex | 15 | 24.19 |

TABLE 4

| Materials | Parts (Dry) | Parts (Wet) |
| --- | --- | --- |
| Deionized water | — | 68.9 |
| Sodium chloride | 0.56 | 0.56 |
| Modified acrylic polymer, Ultrez 21, Lubrizol | 0.75 | 0.75 |
| Potassium hydroxide | 0.56 | 5.6 |
| Compounded synthetic latex | 15 | 24.19 |

Example 2

An article that resists microbial growth is prepared. The article has a surface which comprises a material that is subject to swelling when contacted with a swelling agent. At least a portion of the substrate, which is constructed of a nonconducting material, is contacted with an aqueous solution containing an oxidizing agent and alcohol or other water-miscible solvent which swells the surface of the article. The portion of the substrate thus treated is contacted with an aqueous activation solution; followed by chemically depositing a silver layer of at least 2-2000 Angstroms in thickness, or more, by treating the activated surface with an aqueous deposition solution of at least one salt of silver in the presence of a deposition control agent, the depositing being conducted for sufficient time to deposit a silver layer of specified thickness. At least one of the aqueous activation solution or the aqueous deposition solution includes an alcohol or other water-miscible solvent that swells the surface of the article. After deposition of the silver layer, the surface is optionally rinsed in demineralized water and dried, optionally with assistance of elevated temperature, circulating air or other gas, or reduced humidity. Rinsing and drying steps can be conducted between activation, oxidation, and/or deposition steps.

Example 3

An article that resists microbial growth is prepared. At least a portion of the surface area of an article which article is constructed of a nonconducting material is activated; then the activated surface is treated with an alcoholic solution capable of oxidizing and/or swelling the surface. A silver layer of 2-2000 Angstroms thickness or more is chemically deposited by treating the activated surface with an aqueous solution of at least one salt of silver in the presence of a deposition control agent, the depositing being conducted for only sufficient time to deposit a silver layer of suitable thickness. Rinsing and drying steps can be conducted between activation, oxidation, and/or deposition steps.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:
1. A method for preparing an antimicrobial medical device, comprising:
provide a nonconducting material;
treating a surface of the nonconducting material by depositing a superabsorbent polymer on the surface and exposing the surface to a swelling agent such that the surface swells to a larger size;

depositing silver metal by exposing the surface to an aqueous solution of a silver salt in a presence of a deposition control agent; and treating the silver metal with a stabilizing amount of one or more metals selected from the group comprising platinum group metals and gold, whereby an adhesive, thin, uniform, transparent, antimicrobial, biocompatible coating comprising silver metal is obtained.

2. The method of claim 1, wherein the depositing a superabsorbent polymer on the surface and the exposing the surface to a swelling agent are conducted simultaneously.

3. The method of claim 1, wherein the depositing a superabsorbent polymer on the surface and exposing the surface to a swelling agent are conducted sequentially.

4. The method of claim 1, wherein the swelling agent is an alcohol and/or a water-miscible solvent.

5. The method of claim 4, wherein the alcohol is selected from a group comprising methanol, ethanol, isomers of propanol, isomers of butanol, isomers of pentanol, and combinations thereof.

6. The method of claim 4, wherein the water-miscible solvent is selected from a group comprising acetone, tetrahydrofuran, dimethylformamide, dimethlysulfoxide, acetonitrile, and combinations thereof.

7. The method of claim 1, wherein treating the surface and depositing silver metal are conducted simultaneously, wherein the swelling agent is included in the aqueous solution of a silver salt.

8. The method of claim 1, wherein treating the surface and depositing silver metal are conducted sequentially, wherein the swelling agent is included in a different solution from the aqueous solution of a silver salt.

9. The method of claim 1, wherein the swelling agent is included in a different solution from the aqueous solution of a silver salt, and wherein a same or different swelling agent is included in the aqueous solution of a silver salt.

10. A method for coating a device, comprising:
providing a nonconducting material;
treating a surface of the nonconducting material by depositing a superabsorbent polymer on the surface;
depositing silver metal by exposing the surface to an aqueous solution of a silver salt in a presence of a deposition control agent; and
treating the silver metal with a stabilizing amount of one or more metals selected from the group comprising platinum group metals and gold, whereby an adhesive, thin, uniform, antimicrobial, biocompatible coating comprising silver metal is obtained.

11. The method of claim 10, further comprising exposing the surface to a swelling agent after depositing the superabsorbent polymer on the surface and before depositing the silver metal.

12. The method of claim 11, further comprising waiting for the surface to swell to a larger size after exposing the surface to the swelling agent and before depositing the silver metal.

13. The method of claim 10, wherein the superabsorbent polymer is capable of imbibing deionized water at a capacity of between 10-1000 g/g.

14. A method for preparing an antimicrobial medical device, comprising:
providing a nonconducting material;
treating a surface of the nonconducting material by simultaneously depositing a superabsorbent polymer on the surface and exposing the surface to a swelling agent such that the surface swells to a larger size;
depositing silver metal by exposing the surface to an aqueous solution of a silver salt in a presence of a deposition control agent; and
treating the silver metal with a stabilizing amount of one or more metals selected from a group comprising platinum group metals and gold, whereby an adhesive, thin, uniform, transparent, antimicrobial, biocompatible coating comprising silver metal is obtained.

15. A method for preparing an antimicrobial medical device, comprising:
providing a nonconducting material;
treating a surface of the nonconducting material by depositing a superabsorbent polymer on the surface;
depositing silver metal by exposing the surface to an aqueous solution of a silver salt in a presence of a deposition control agent; and
treating the silver metal with a stabilizing amount of one or more metals selected from a group comprising platinum group metals and gold, whereby an adhesive, thin, uniform, transparent, antimicrobial, biocompatible coating comprising silver metal is obtained.

* * * * *